United States Patent [19]

Barnes

[11] Patent Number: 5,616,494
[45] Date of Patent: Apr. 1, 1997

[54] *THERMUS AQUATICUS* DNA POLYMERASE LACKING THE N-TERMINAL 235 AMINO ACIDS OF TAQ DNA POLYMERASE

[76] Inventor: Wayne M. Barnes, Chesterfield, Mo

[21] Appl. No.: 274,205

[22] Filed: Jul. 11, 1994

Related U.S. Application Data

[63] Continuation of Ser. No. 62,712, May 17, 1993, abandoned, which is a continuation of Ser. No. 594,637, Oct. 5, 1990, abandoned.

[51] Int. Cl.$^6$ ................. C12N 1/21; C12N 9/12
[52] U.S. Cl. .................. 435/252.3; 435/320.1; 435/194; 435/325; 530/350; 530/825; 536/23.2; 930/240; 935/10
[58] Field of Search .................. 435/194, 69.1, 435/172.1, 240.1, 252.3, 320.1; 530/350, 820, 825; 930/240; 935/10

[56] References Cited

U.S. PATENT DOCUMENTS

| | | | |
|---|---|---|---|
| 4,889,818 | 12/1989 | Gelfand | 435/194 |
| 5,079,352 | 1/1992 | Golfand et al. | 536/27 |
| 5,108,892 | 4/1992 | Burke et al. | 435/6 |

FOREIGN PATENT DOCUMENTS

| | | |
|---|---|---|
| 8906691 | 7/1989 | WIPO . |
| 9102090 | 2/1991 | WIPO . |

OTHER PUBLICATIONS

Jacobsen, H. et al. Eur. J. Biochem. 45:623–627. 1974.
Maniatis, T. et al., "Molecular Cloning, a Laboratory Manual" published 1982 by McGraw–Hill (N.Y.), see pp. 108 and 114.
Innis et al., Proc. Natl. Acad. Sci. USA 85:9436–9440, 1988.
Lawyer et al., J. Biol. Chem. 264:6427, 1989.
Promega (advertising pages).
Perkin–elmer Cetus (advertising pages).

*Primary Examiner*—Garnette D. Draper
*Assistant Examiner*—Lorraine M. Spector
*Attorney, Agent, or Firm*—Lyon & Lyon

[57] ABSTRACT

A vector which includes nucleic acid which encodes a DNA polymerase having an identical amino acid sequence to that of the DNA polymerase of *Thermus aquaticus* termed Taq DNA polymerase, except that it lacks the N-terminal 235 amino acids of Taq DNA polymerase.

6 Claims, 1 Drawing Sheet

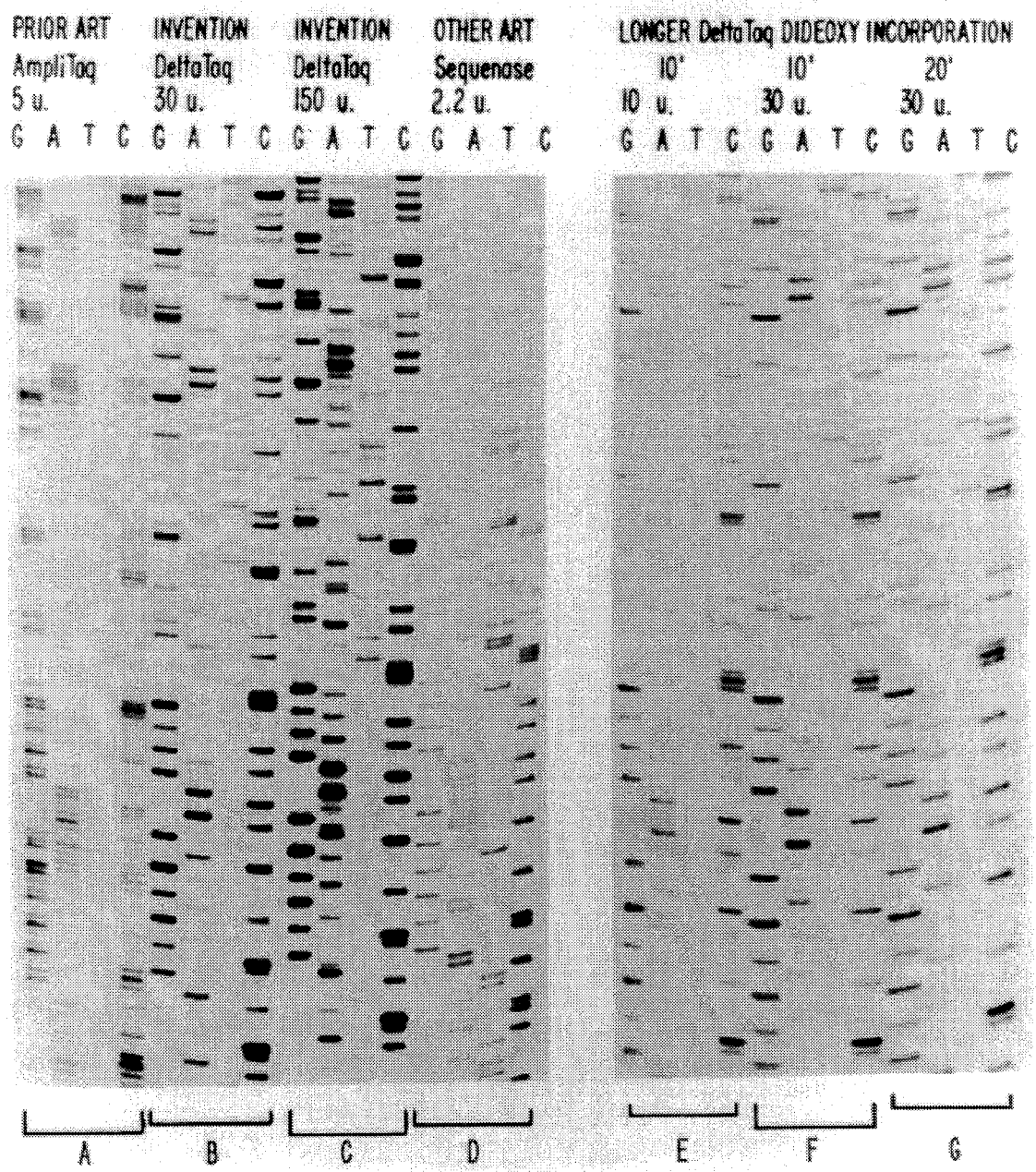

THERMUS AQUATICUS DNA POLYMERASE LACKING THE N-TERMINAL 235 AMINO ACIDS OF TAQ DNA POLYMERASE

This application is a continuation of application Ser. No. 08/062,712, filed May 17, 1993, abandoned, which is a continuation of application Ser. No. 07/594,637, filed Oct. 5, 1990, abandoned.

BACKGROUND OF THE INVENTION

This invention relates to thermostable DNA polymerases useful for DNA sequencing.

Innis et al., Proc. Natl. Acad. Sci. USA 85:9436–9440, 1988 state that a DNA polymerase from *Thermus aquaticus* (termed Taq or Taq DNA polymerase) is useful for DNA sequencing.

Lawyer et al., J. Biol. Chem. 264:6427, 1989 describe the isolation and cloning of DNA encoding Taq. The DNA and amino acid sequences described in this publication define the Taq gene and Taq DNA polymerase as those terms are used in this application.

Gelfand et al., U.S. Pat. No. 4,889,818, describe the isolation and expression of Taq and state that:

It has also been found that the entire coding sequence of the Taq polymerase gene is not required to recover a biologically active gene product with the desired enzymatic activity. Amino-terminal deletions wherein approximately one-third of the coding sequence is absent have resulted in producing a gene product that is quite active in polymerase assays.

Thus, modifications to the primary structure itself by deletion, addition, or alteration of the amino acids incorporated into the sequence during translation can be made without destroying the activity of the protein.

In the particular case of Taq polymerase, evidence indicates that considerable deletion at the N-terminus of the protein may occur under both recombinant and native conditions, and that the activity of the protein is still retained. It appears that the native proteins isolated may be the result of proteolytic degradation, and not translation of a truncated gene. The mutein produced from the truncated gene of plasmid pFC85 [containing a 2.8 kb HindIII-Asp718 restriction fragment; where the HindIII site is at codons 206 and 207] is, however, fully active in assays for DNA polymerase, as is that produced from DNA encoding the full-length sequence. Since it is clear that certain N-terminal shortened forms are active, the gene constructs used for expression of the polymerase may also include the corresponding shortened forms of the coding sequence.

SUMMARY OF THE INVENTION

The invention features a vector which includes nucleic acid encoding a DNA polymerase having an identical amino acid sequence to that of the DNA polymerase of *Thermus aquaticus*, termed Taq DNA polymerase, except that it lacks the N-terminal 235 amino acids of wild-type Taq DNA polymerase (see Lawyer et al., supra). This DNA polymerase is designated ΔTaq (Delta Taq) in this application.

Applicant has discovered that the N-terminal 235 amino acids of Taq polymerase can be removed without loss of the DNA polymerase activity or thermal stability of the polymerase. The ΔTaq polymerase is still stable to heating at high temperatures, but has little or no 5'-exonuclease activity as determined by DNA sequencing experiments. Because of the lack of the associated 5'-exonuclease of Taq, the ΔTaq polymerase is significantly superior to wild-type Taq polymerase for DNA sequencing. The ΔTaq polymerase can be used with little consideration being paid to the length of time or the buffer conditions in which the extension reactions of the DNA sequencing reaction are performed.

In preferred embodiments, the vector is that nucleic acid present as plasmid pWB253 deposited as ATCC No. 68431 or a host cell containing such a vector.

In a related aspect, the invention features a purified DNA polymerase having an amino acid sequence essentially identical to Taq but lacking the N-terminal 235 amino acids, e.g., ΔTaq. By "purified" is meant that the polymerase is isolated from a majority of host cell proteins normally associated with it, preferably the polymerase is at least 10% (w/w) of the protein of a preparation, even more preferably it is provided as a homogeneous preparation, e.g., a homogeneous solution.

ΔTaq appears to be less processive than wild-type Taq. More units of DNA polymerase are necessary for ΔTaq to complete a PCR amplification reaction.

BRIEF DESCRIPTION OF THE FIGURES

The drawing is a reproduction of an autoradiogram formed from a sequencing gel.

DESCRIPTION OF THE PREFERRED EMBODIMENT

The following is intended to demonstrate an example of the method and materials suitable for practice of this invention. It is offered by way of illustration and is not limiting to the invention.

Construction of an expressible gene for ΔTaq

In order to construct the ΔTaq DNA polymerase gene having an N-terminal sequence shown as nucleotide sequence 1, and a C-terminal sequence shown as nucleotide sequence 2, the following procedure was followed.

The mutated gene was amplified from 0.25 ug of total *Thermus aquaticus* DNA using the polymerase chain reaction (PCR, Saiki et al., Science 239:487, 1988) primed by the following two synthetic DNA primers: (a) a 27mer (shown as nucleotide sequence 3) with homology to the wild-type DNA starting at wild-type base pair 705; this primer is designed to incorporate a NcoI site into the product amplified DNA; (b), a 33mer (shown as nucleotide sequence 4) spanning the stop codon on the other strand of the wild-type gene encoding Taq, and incorporating a HindIII site into the product DNA.

The buffer for the PCR reaction was 10 mM Tris HCl pH 8.55, 2.5 mM $MgCl_2$, 16 mM $(NH_4)_2SO_4$, 150 ug/ml BSA, and 200 uM each dNTP. The cycle parameters were 2' 95°, 2' 65°, 5' 72°.

In order to minimize the mutations introduced by PCR (Saiki et al., supra), only 10 cycles of PCR were performed before phenol extraction, ethanol precipitation, and digestion with the restriction enzymes NcoI and HindIII.

The product NcoI and HindIII fragment was cloned into plasmid pWB250 which had been digested with NcoI, HindIII, and calf intestine alkaline phosphatase. The backbone of this plasmid, previously designated pTAC2 and obtained from J. Majors, carries the following elements in counter-clockwise direction from the PvuII site of pBR322 (an apostrophe ' designates that the direction of expression is clockwise instead of counter clockwise): a partial lacZ' sequence, lacI', lacPUV5 (orientation not known), two copies of the tac promoter from PL Biochemicals Pharmacia- LKB; catalog no. 27-4883), the T7 gene 10 promoter and start codon modified to consist of a NcoI site, a HindIII site, the TrpA terminator (PL no. 27-4884-01), an M13 origin of replication, and the ampR gene of pBR322. Expression of the cloned gene is induced by 0.1 mM IPTG.

Three of twelve ampicillin resistant colonies arising from the cloning proved to contain the desired fragment, based on their size by toothpick assay (Barnes, Science 195:393, 1977), their ability to give rise to the 1800 bp target fragment by colony PCR, and high levels of IPTG-induced DNA polymerase activity in an extract created by heating washed cells from 0.5 ml of culture at 80° C. (fraction I, as described below for an early step in the purification method). The first of these plasmids was designated pWB253 and used for the preparative production of ΔTaq.

Purification of large amounts of Mutant Taq

One liter of late log phase culture of pWB253 in *E. coli* host strain X7029 (wild-type *E. coli* having a deletion X74 covering the lac operon) was distributed among four liters of fresh rich culture medium containing 0.1 mM IPTG, and incubation with shaking was continued at 37° C. for 12 hours. The total 5 liters was collected by centrifugation and resuspended in Lysis Buffer (20 mM Tris-HCl pH 8.55, 10 mM MgCl$_2$, 16 mM (NH$_4$)$_2$SO$_4$, 0.1% NP40, 0.1% Tween20, and 1 mM EDTA). To 300 ml of cell suspension were added 60 mg lysozyme and the cells were incubated at 5°–10° C. with occasional swirling for 15 minutes. The cell suspension was then heated rapidly to 80° C. by swirling it in a boiling water bath, and the cells maintained at 80°–81° C. for 17 minutes. After this treatment, which is expected to inactivate most enzymes, the cells were cooled to 37° C. in an ice bath, and 2 ml of protease inhibitor (100 mM PMSF in isopropanol) were added. The cells were distributed into centrifuge bottles and centrifuged 15 minutes at 15,000 in a Sorval SS-34 rotor at 2° C. The supernatant was designated fraction I.

Detergents NP40 and Tween20 were present at 0.01% to 0.5% (usually 0.1%) at all times and in all buffers and solutions to which the enzyme was exposed. Unless otherwise noted all buffers also contained Tris-HCl and DTT as described for the storage buffer below.

After rendering fraction I 0.25M in NaCl, ten percent Polymin-P (polyethylene-imine) was added dropwise to precipitate nucleic acids. To determine that adequate Polymin-P had been added, and to avoid addition of more than the minimum amount necessary, 0.5 ml of centrifuged extract was periodically tested by adding a drop of Polymin-P, and only if more precipitate formed was more Polymin-P added to the bulk extract. Centrifugation of the extract then removed most of the nucleic acids.

Chromatography with Bio-Rex 70 (used by Joyce and Grindley, Proc. Natl. Acad. Sci. USA 80:1830, 1983) was unsuccessful. The polymerase activity did not bind at all, even when the enzyme was diluted to a salt concentration of 0.1M. The reasons for this lack of binding to Bio-Rex 70 were not investigated further at this time. Rather, the flow-through from Bio-Rex 70 was applied to another chromatography medium.

Successful chromatography was then carried out with heparin agarose. The extract, by now diluted to 1 liter, was stirred with 50 ml of heparin agarose, and then the agarose packed lightly into a column. The column was washed with 0.1M NaCl, and the enzyme eluted with 1M NaCl. The peak of polymerase activity (12 ml) was then dialyzed against 50% glycerol storage buffer (50% glycerol (v/v), 100 nM KCl, 20 mM Tris-HCl pH 8.55, 0.1 mM EDTA, 1 mM DTT, 0.5% Tween and 20, 0.5% NP40). The final yield of enzyme was 6 ml at a concentration of 300,000 units per ml (see below). An aliquot of enzyme was diluted 10-fold into storage buffer, and this working strength enzyme was designated KT5.

One unit of enzyme is defined as the amount of enzyme that incorporates 10 nmoles of deoxytriphosphates into acid insoluble material in 30 minutes at 74° C. Actual assay times were 5 minutes or 10 minutes (with appropriate extrapolation to 30 minutes). Titred full-length Taq DNA polymerase (AmpliTaq; commercially available at 5 commercial units/ul; one commercial unit is believed to be equivalent to one of the units defined in this application) was used as a standard. The assay buffer was 20 mM Tris-HCl pH 7.8, 8 mM MgCl$_2$, 0.1 mg/ml BSA, 5 mM DTT, 4% glycerol, 100 uM each dATP, dTTP, and dCTP, 25 uM [$_3$H]dTTP (400 cmp/pmole), and 160 ug/ml activated calf thymus DNA (commercially available; Pharmacia).

Sequencing Procedure

Dideoxy sequencing with the above ΔTaq is summarized below. It follows basically the procedure described by Innis et al., Proc. Natl. Acad. Sci. USA 85:9436, 1988. The reactions were performed in microtitre wells.

In the labelling extension reaction, 24 µl of Lg mix (14 µl of water, 3 µl of 10 X ΔTaq buffer (20 mM Tris HCl pH 8.5 at 25° C., 10 mM MgCl$_2$, 2 mM MnCl$_2$, 10 mM isocitrate, and 16 mM ammonium sulphate (the ammonium sulphate may be replaced with 50 mM KCl or with water), 3 µl 10 mM dTTP, 1 µl 10 mM dGTP, and 3 µl 10 mM dCTP) was added to 3 µl of template (0.5–1.0 picomole) and 2 µl (2 picomole) primer. These solutions were vortexed, spun down, and allowed to anneal by heating to 70° C. and cooling to 45° C. $^{32}$p dATP (400 mCi/µmole; 1 mCi/ml is equivalent to 2.5 µM) was dried down and resuspended in the DNA solution and 1 µl ΔTaq (5 units) added. The solution was warmed to 37° C. for 45 seconds and chilled on ice. Four reaction aliquots were taken from this reaction mixture and placed into microtitre wells containing 4 µl of solution containing 2 µl 4 X dXTP and 2 µl of one of four 4 X dd stock solutions. 4 X dXTP consists of 120 µM of all 4 dNTP's, 0.2% Tween 20, and 0.2% Nonidet P-40. Each of the 4 X dd stock solution contains either 720 µM ddA, 360 µM ddC, 72 µM ddG, or 360 µM ddT (or water as a control). The 4 X dXTP and the 4 X dd solutions were premixed at a 1:1 ratio so that 4 µl of the resulting solution could be added to each of the 4 DNA reaction aliquots. The solutions were mixed, the microtitre wells covered with tape and warmed to 70°–75° C. for ten minutes. (Incubation may be continued for twenty or thirty minutes if desired.) The microtitre wells were then dried under vacuum (after removal of the tape) and 12 µl of blue formamide buffer added. The wells were then heated for thirty seconds to 90° C. and ⅕ of the material loaded on a gel.

The Figure is one example of the results of such a sequencing reaction. In the Figure the results obtained with AmpliTaq (wild-type Taq) DNA polymerase are compared with ΔTaq and Sequenase® T7 DNA polymerase. ΔTaq has an insignificant level of 5'-exonuclease activity since it gives rise to few or no triplet bands on the sequencing gel compared to AmpliTaq DNA polymerase.

The sequencing procedure above was followed identically for all experiments except for the differences in enzyme, enzyme units added, and incubation times noted on the Figure. The incubation time for the experimental results shown in lanes A–D was 3 minutes, in lanes E and F it was 10 minutes, and in lane G it was 20 minutes. Sequenase® DNA polymerase was used at lower temperatures and under the conditions described by Tabor and Richardson, Proc. Nat. Acad. Sci. USA 84: 4767, 1987. The template was single-stranded DNA encoding an artificial gene for scorpion toxin AaIT. The primer was the 'reverse' lac primer which spans the start codon of lacZ on the vector pBs– (Bluescribe 'minus', from Stratagene)

From the Figure it is clear that 5 commercial units (approximately 30 units, as defined above) of AmpliTaq DNA polymerase in a short extension reaction (3 minutes) gives very poor sequencing data; whereas 30 units or even 150 units of ΔTaq gives excellent data, even after a long (10 or 20 minute) extension reaction, and compares favorably with Sequenase® DNA polymerase.

Deposit

Strain pWB253/X7029 was deposited with the American Type Culture Collection, Maryland, on Oct. 4, 1990 and assigned the number ATCC 68431. Applicant acknowledges its responsibility to replace this culture should it die before the end of the term of a patent issued hereon, 5 years after the last request for a culture, or 30 years, whichever is the longer, and its responsibility to notify the depository of the issuance of such a patent, at which time the deposits will be made available to the public. Until that time the deposits will be made available to the Commissioner of Patents under the terms of 37 C.F.R. Section 1-14 and 35 U.S.C. Section 112. All restrictions on the availability to the public of the deposited material will be irrevocably removed upon the granting of the patent.

Other embodiments are within the following claims.

I claim:

1. A vector comprising a nucleic acid molecule encoding a DNA polymerase having the amino acid sequence of the Taq DNA polymerase of *Thermus aquaticus* lacking the N-terminal 235 amino acids of Taq DNA polymerase.

2. The vector of claim 1, said nucleic acid molecule being identical to that present in the plasmid pWB253 present in the host cell deposited as ATCC No. 68431.

3. A host cell comprising the vector of claim 1.

4. The host cell of claim 3 deposited as ATCC No. 68431.

5. A purified DNA polymerase having the amino acid sequence of the Taq DNA polymerase of *Thermus aquaticus* lacking the N-terminal 235 amino acids of Taq DNA polymerase.

6. The purified DNA polymerase of claim 5, said polymerase being provided as a homogeneous preparation.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 80
( B ) TYPE: nucleic acid
( C ) STRANDEDNESS: single
( D ) TOPOLOGY: linear ( i i ) SEQUENCE DESCRIPTION: SEQ ID NO: 1:

AACGGTTTCC CTCTAGAAAT AATTTGTTT AACTTTAAGA AGGAGATATA TCCATGGACG  60

ATCTGAAGCT CTCCTGGGAC  80

( 2 ) INFORMATION FOR SEQ ID NO: 2:

( i ) SEQUENCE CHARACTERISTICS:
( A ) LENGTH: 160
( B ) TYPE: nucleic acid
( C ) STRANDEDNESS: single
( D ) TOPOLOGY: linear ( i i ) SEQUENCE DESCRIPTION: SEQ ID NO: 2:

GAGGTCATGG AGGGGGTGTA TCCCCTGGCC GTGCCCCTGG AGGTGGAGGT GGGGATAGGG  60

GAGGACTGGC TCTCCGCCAA GGAGTGAAGC TTATCGATGA TAAGCTGTCA AACATGAGAA  120

TTAGCCCGCC TAATGAGCGG GCTTTTTTTT AATTCTTGAA  160

( 2 ) INFORMATION FOR SEQ ID NO: 3:

( i ) SEQUENCE CHARACTERISTICS:
( A ) LENGTH: 27
( B ) TYPE: nucleic acid
( C ) STRANDEDNESS: single
( D ) TOPOLOGY: linear ( i i ) SEQUENCE DESCRIPTION: SEQ ID NO: 3:

GTGTCCATGG ACGATCTGAA GCTCTCC  27

( 2 ) INFORMATION FOR SEQ ID NO: 4:

( i ) SEQUENCE CHARACTERISTICS:
( A ) LENGTH: 33
( B ) TYPE: nucleic acid
( C ) STRANDEDNESS: single
( D ) TOPOLOGY: linear ( i i ) SEQUENCE DESCRIPTION: SEQ ID NO: 4:

GCGAAGCTTC ACTCCTTGGC GGAGAGCCAG TCC  33